United States Patent
Asakawa et al.

(10) Patent No.: US 6,294,693 B1
(45) Date of Patent: Sep. 25, 2001

(54) PRODUCTION PROCESS FOR ETHER CARBOXYLATE SALT

(75) Inventors: Miaki Asakawa, Himeji; Yasutaka Sumida, Neyagawa; Mitsuhiro Kitajima, Suita, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/323,887

(22) Filed: Jun. 2, 1999

(30) Foreign Application Priority Data

Jun. 10, 1998 (JP) .................................................. 10-162569
Jun. 12, 1998 (JP) .................................................. 10-165119

(51) Int. Cl.⁷ .............................................. C07C 59/125
(52) U.S. Cl. ........................................ 562/583; 587/588
(58) Field of Search .................... 562/583, 588, 562/587

(56) References Cited

U.S. PATENT DOCUMENTS

| | | | |
|---|---|---|---|
| 3,692,685 | * | 9/1972 | Lamberti et al. ...................... 510/478 |
| 3,914,297 | * | 10/1975 | Lamberti et al. ...................... 562/583 |
| 4,118,420 | * | 10/1978 | Lannert ............................... 560/583 |
| 4,663,071 | * | 5/1987 | Bush et al. ........................... 510/361 |
| 5,801,277 | * | 9/1998 | Sumida et al. ......................... 562/583 |

FOREIGN PATENT DOCUMENTS

| | | |
|---|---|---|
| 0808656 | 11/1997 | (EP) . |
| A-10066868 | 3/1990 | (JP) . |
| 10120619 | 5/1998 | (JP) . |

OTHER PUBLICATIONS

"Synthesis of Poly(Hydroxy)Carboxylates—Part II, Addition of Polyols to Maleate Homogeneously Catalysed by Multivalent Metal Ions"Westrenen et al.; *Tetrahedron*, vol. 46, No. 16, 1990, pp. 5741–5758.

"Lanthanide(III)–catalysed Addition of Glycolate to Maleate, Investigation of Intermediates Using Multinuclear Magnetic Resonance Spectroscopy"; *Journal of Chemical Society*, Dalton Transactions, No. 11, Nov. 1988; pp. 2723–2728.

Chemical Abstract 75, 89458 (1971).

"Lanthanide (III)–catalysed Addition of Glycolate to Maleate; Investigation Intermediates using Multi–Nuclear Magnetic Resonance Spectroscopy"; J. Chem. Dalton Trans., 2723–2728 (1998).

* cited by examiner

*Primary Examiner*—Gary Geist
*Assistant Examiner*—Taylor V Oh
(74) *Attorney, Agent, or Firm*—Roylance, Abrams, Berdo & Goodman, L.L.P.

(57) ABSTRACT

The present invention provides a production process for an ether carboxylate salt in which process the ether carboxylate salt is obtainable with a good yield, and the amount of expensive catalyst, as used, can be saved, and the recovery of the catalyst is easy. The production process for an ether carboxylate salt comprises the etherification step of reacting a hydroxyl-group-containing organic compound and a carboxyl-group-containing organic compound in an aqueous medium in the presence of a catalyst containing a rare earth element, wherein the carboxyl-group-containing organic compound is at least one compound selected from the group consisting of carboxyl-group-containing unsaturated organic compounds and carboxyl-group-containing epoxy compounds. This process is characterized in that the pH of the aqueous medium is in the range of 9~13, but not including 9, and in that the amount of the catalyst, as used, is in the range of 0.0001~0.4 mol per 1 mol of the carboxyl-group-containing organic compound. After the etherification step, the rare earth element is separated and recovered in the form of a water-insoluble salt. In the etherification step, the resultant ether compound is deposited in the course of the reaction.

11 Claims, No Drawings

PRODUCTION PROCESS FOR ETHER CARBOXYLATE SALT

BACKGROUND OF THE INVENTION

A. Technical Field

The present invention relates to a production process for an ether carboxylate salt involving the use of a catalyst containing a rare earth element.

B. Background Art

A conventional production process for an ether carboxylate salt comprises the etherification step of reacting a hydroxyl-group-containing organic compound and a carboxyl-group-containing organic compound, wherein the carboxyl-group-containing organic compound is at least one compound selected from the group consisting of carboxyl-group-containing unsaturated organic compounds and carboxyl-group-containing epoxy compounds.

Sodium carboxymethoxysuccinate, which is one of the ether carboxylate salts, is useful as a phosphorus-free detergent builder and obtainable by a process comprising the step of reacting maleic anhydride and glycolic acid in an aqueous medium in the presence of calcium hydroxide (Chemical Abstract, 75, 89458 (1971)).

It is reported that the lanthanum (III) ion is also usable as the catalyst in place of the calcium ion in the same homogeneous reaction as above (Jeroen van Westrenen et al., J. Chem. Soc. Dalton Trans., 2723–2728 (1988)).

Processes involving the use of rare earth element ions such as lanthanum ion as the catalyst are more excellent in respect to higher activity of the catalyst, and further, higher selectivity and yield of the aimed product when compared with processes involving the use of the calcium ion.

However, the above conventional processes involving the use of rare earth element ions have problems as follows.

In those processes, a large amount of catalyst is used to smoothly run the reaction. However, the rare earth element is expensive, so it is desired to save the amount of the rare earth element, as used, or to recover and reuse the catalyst as already used for the reaction, for the purpose of saving the production cost.

The etherification reaction in a solution generally has problems in that: as the reaction advances, the concentration of raw compounds gradually lowers, so the reaction becomes difficult to advance, and the aimed ether compound therefore cannot be obtained with a high yield. The cause of such problems is that the ether compound, as once obtained, easily reverts to the raw compounds due to the reverse reaction, or that a side reaction competing with the reverse reaction occurs to give a by-product.

SUMMARY OF THE INVENTION

A. Objects of the Invention

An object of the present invention is to save the amount of expensive catalyst as used.

Another object of the present invention is to facilitate the recovery of the expensive catalyst.

Yet another object of the present invention is to suppress the reverse reaction or side reaction, thus obtaining an ether compound with a high yield.

B. Disclosure of the Invention

To achieve the above first object, the present invention is characterized in that: in the etherification step, the pH of the aqueous medium is in the range of 9~13, but not including 9, and the amount of the catalyst, as used, is in the range of 0.0001~0.4 mol per 1 mol of the carboxyl-group-containing organic compound.

To achieve the above second object, in the present invention, the rare earth element is separated and recovered in the form of a water-insoluble salt after the reaction.

To achieve the above third object, in the present invention, the resultant ether carboxylic acid or its salt is deposited in the course of the reaction.

These and other objects and the advantages of the present invention will be more fully apparent from the following detailed disclosure.

DETAILED DESCRIPTION OF THE INVENTION

The above Jeroen van Westrenen et al.'s process is a process comprising the step of reacting sodium glycolate and sodium maleate at the pH of 5~9 in water in the presence of lanthanum trichloride, thus obtaining carboxymethoxysuccinate salts (sodium salt and lanthanum salt).

In the course of the study of processes to solve the above problems, the present inventors traced the above Jeroen van Westrenen et al.'s experiment and found that the carboxymethoxysuccinate salt, which is a reaction product, is not in the form of a sodium salt, but mainly in the form of a lanthanum salt at the pH of 5~9, and that the free lanthanum ion has catalytic activity, whereas the above lanthanum salt does not. Thus, the inventors concluded that the reason why a large amount of catalyst is necessary at the pH of 5~9 is because the active free lanthanum ion is gradually consumed by a reaction product. Then, the inventors studied a process to prevent the consumption of the active free lanthanum ion, and as a result, completed the present invention by finding that if the pH is high, the carboxymethoxysuccinate salt, which is a reaction product, has the form of not a lanthanum salt, but a sodium salt, so the active free lanthanum ion is not consumed during the reaction, and thus the amount thereof, as used, can be saved.

Next, the recovery of the lanthanum ion is usually carried out by allowing an ion-exchange resin to adsorb the lanthanum ion, and its recovery efficiency is low, and the ion-exchange resin is also expensive. Furthermore, the reuse of the lanthanum ion, as adsorbed to the ion-exchange resin, necessitates the step of desorbing the lanthanum ion from the ion-exchange resin by using a large quantity of mineral acid (e.g. sulfuric acid, hydrochloric acid), so there are problems in that such a process inevitably involves a high cost. Thus, the present inventors intended to solve such problems by separating and recovering the rare earth element in the form of a water-insoluble salt after the reaction.

The present inventors diligently studied and made experiments to intend to suppress the reverse reaction or side reaction. As a result, the inventors completed the present invention by finding that: if the ether compound, which is a product, is deposited in the course of the reaction, the ether compound is removed from the liquid-phase reaction system, so the concentration of the raw compounds becomes higher than that in a state before the deposition (state where the ether compound is present in the reaction system), and therefore, the etherification reaction is promoted, and the side reaction is inhibited from occurring.

Hereinafter, the present invention is described in detail.

The production process for an ether carboxylate salt, according to the present invention, comprises the etherification step of reacting raw compounds, which step is carried out in an aqueous medium in the presence of a catalyst containing a rare earth element. The raw compounds include a hydroxyl-group-containing organic compound and a carboxyl-group-containing organic compound, wherein the carboxyl-group-containing organic compound is at least one compound selected from the group consisting of carboxyl-group-containing unsaturated organic compounds and carboxyl-group-containing epoxy compounds.

Examples of the hydroxyl-group-containing organic compound include hydroxycarboxylic acid compounds, polyhydric alcohol compounds, higher alcohol compounds with 6 to 22 carbon atoms, and saccharides. These hydroxyl-group-containing organic compounds are more specifically illustrated as follows:

Hydroxycarboxylic Acid Compounds (a) Compounds of the following general formula (1):

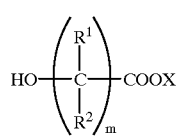

(1)

wherein: $R^1$ and $R^2$, independently of each other, denote a hydrogen atom or an alkyl with 1 to 3 carbon atoms; X denotes a hydrogen atom, an alkaline metal atom, an alkaline earth metal atom, an ammonium group, an alkylammonium group, or an alkanolammonium group; and m denotes an integer of 1 to 10. Typical examples are glycolic acid, β-hydroxypropionic acid, and lactic acid.

(b) Compounds of the following general formula (2):

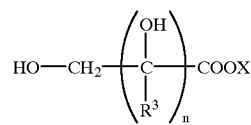

(2)

wherein: $R^3$ denotes a hydrogen atom or an alkyl with 1 to 3 carbon atoms; n denotes an integer of 1 to 10; and X is the same as that in general formula (1) above. Typical examples are glyceric acid and gluconic acid.

(c) Compounds of the following general formula (3):

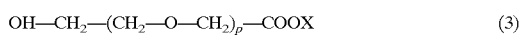

OH—CH$_2$—(CH$_2$—O—CH$_2$)$_p$—COOX      (3)

wherein: p denotes an integer of 1 to 10; and X is the same as that in general formula (1) above. Typical examples are diethylene glycol monocarboxylates.

(d) Compounds of the following general formula (4):

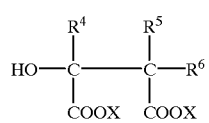

(4)

wherein: $R^4$ and $R^5$, independently of each other, denote a hydrogen atom or an alkyl with 1 to 3 carbon atoms; $R^6$ denotes a hydrogen atom, an alkyl with 1 to 8 carbon atoms, or hydroxyl; and X is the same as that in general formula (1) above. Typical examples are malic acid and tartaric acid.

(e) Compounds of the following general formula (5):

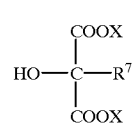

(5)

wherein: $R^7$ denotes a hydrogen atom or an alkyl with 1 to 3 carbon atoms; and X is the same as that in general formula (1) above. A typical example is tartronic acid.

(f) Compounds of the following general formula (6):

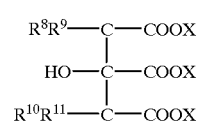

(6)

wherein: $R^8$, $R^9$, $R^{10}$, and $R^{11}$, independently of each other, denote a hydrogen atom or an alkyl with 1 to 3 carbon atoms; and X is the same as that in general formula (1) above. A typical example is citric acid.

Polyhydric Alcohol Compounds (a) Compounds of the following general formula (7):

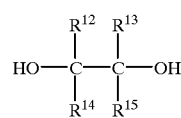

(7)

wherein $R^{12}$ to $R^{15}$, independently of each other, denote a hydrogen atom or an alkyl with 1 to 3 carbon atoms. Typical examples are ethylene glycol and isopropylene glycol.

(b) Products by condensation of 2 to 10 molecules of compounds of general formula (7) above:

A typical example thereof is diethylene glycol.

(c) Glycerol and derivatives therefrom:

Typical examples thereof are glycerol, diglycerol, and polyglycerol.

(d) Sorbitol, 1,4-sorbitan, pentaerythritol, dipentaerythritol.

Higher Alcohol Compounds with 6 to 22 Carbon Atoms (R—OH)

Typical examples thereof are alcohols in which R is hexyl, heptyl, octyl, nonyl, decyl, undecyl, lauryl, myristyl, palmityl, stearyl, arachidyl, behenyl, oleyl, linol, linolenyl, or 2-ethylhexyl.

Saccharides

Typical examples thereof are glucose, mannose, galactose, fructose, lactose, and sucrose.

Examples of the carboxyl-group-containing unsaturated organic compound, usable in the etherification reaction, include unsaturated monocarboxylic acids and unsaturated dicarboxylic acids. These carboxyl-group-containing unsaturated organic compounds are more specifically illustrated as follows:

Unsaturated Monocarboxylic Acid Compounds
(a) Compounds of the following general formula (8):

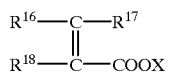
(8)

wherein: $R^{16}$ to $R^{18}$, independently of each other, denote a hydrogen atom or an alkyl with 1 to 10 carbon atoms; and X is the same as that in general formula (1) above. Typical examples are acrylic acid and methacrylic acid.

Unsaturated Dicarboxylic Acid Compounds
(a) Compounds of the following general formula (9):

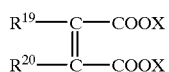
(9)

wherein: $R^{19}$ and $R^{20}$, independently of each other, denote a hydrogen atom or an alkyl with 1 to 10 carbon atoms; and X is the same as that in general formula (1) above. A typical example is maleic acid. The unsaturated dicarboxylic acid may be an anhydrous one.

Examples of the carboxyl-group-containing epoxy compound include the following epoxy compounds:
Compounds of the Following General Formula (10)

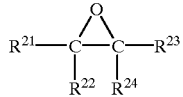
(10)

wherein: $R^{21}$ to $R^{24}$, independently of each other, denote a hydrogen atom, an alkyl with 1 to 10 carbon atoms, or —$(CH_2)_n$—COOX (wherein: n is an integer of 0 to 10; and X is the same as that in general formula (1) above); and at least one of $R^{21}$ to $R^{24}$ is —$(CH_2)_n$—COOX. Typical examples are glycidic acid and epoxysuccinic acid.

A preferable embodiment of the present invention production process is, for example, a process comprising the step of carrying out an etherification reaction of the below-mentioned hydroxyl-group-containing organic compound (A) with the below-mentioned carboxyl-group-containing unsaturated organic compound (B1) and/or carboxyl-group-containing epoxy compound (B2).

The hydroxyl-group-containing organic compound (A) is, for example, at least one compound selected from the group consisting of: hydroxycarboxylic acids, such as glycolic acid, β-hydroxypropionic acid, lactic acid, glyceric acid, gluconic acid, diethylene glycol monocarboxylic acids, malic acid, tartaric acid, tartronic acid, and citric acid; polyhydric alcohols, such as ethylene glycol, isopropylene glycol, diethylene glycol, glycerol, diglycerol, polyglycerol, sorbitol, 1,4-sorbitan, pentaerythritol, and dipentaerythritol; higher alcohols with 6 to 22 carbon atoms; and saccharides, such as glucose, mannose, galactose, fructose, lactose, and sucrose. A preferred one among them is at least one compound selected from the group consisting of glycolic acid, malic acid, tartaric acid, and tartronic acid.

The carboxyl-group-containing unsaturated organic compound (B1) is, for example, at least one compound selected from the group consisting of: unsaturated monocarboxylic acids, such as acrylic acid and methacrylic acid; and unsaturated dicarboxylic acids, such as (anhydrous) maleic acid. Among them, (anhydrous) maleic acid is preferable.

The carboxyl-group-containing epoxy compound (B2) is, for example, at least one compound selected from the group consisting of glycidic acid and epoxysuccinic acid. Among them, epoxysuccinic acid is preferable.

The ratio of the hydroxyl-group-containing organic compound to the carboxyl-group-containing organic compound is not especially limited, but is preferably in the range of 0.5~2, more preferably 0.8~1.2, in terms of (hydroxyl-group-containing organic compound)/(carboxyl-group-containing organic compound) (molar ratio). In the case where the above molar ratio is less than 0.5 or exceeds 2, one of the above raw compounds might remain at the end of the reaction, so the purification step for removing it might be needed.

Examples of the catalyst, usable in the production process of the present invention, include homogeneous catalysts containing rare earth elements. These catalysts are usually in the form, for example, of chlorides, nitrates, sulfates, oxalates, oxides, or hydroxides.

Examples of the rare earth element include: lanthanoid elements, such as lanthanum, cerium, praseodymium, and neodymium; scandium; and yttrium. Among them, lanthanum is preferably used because it is relatively inexpensive and easily available.

The amount of the catalyst, as used, is in the range of usually 0.0001~0.4 mol, preferably 0.0005~0.25 mol, more preferably 0.001~0.1 mol, per 1 mol of the carboxyl-group-containing organic compound. In the case where the amount of the catalyst as used is smaller than 0.0001 mol per 1 mol of the carboxyl-group-containing organic compound, the etherification reaction advances with difficulty. On the other hand, in the case where the amount of the catalyst as used exceeds 0.4 mol, the absolute amount of the catalyst is so large that the recovery thereof is difficult and needs much time and labor, and as a result, the production cost of the ether carboxylate salt is high.

Water is generally used as the aqueous medium usable in the present invention, but, for example, the following might also fitly be used: alcohols, dioxane, tetrahydrofuran, 1,2-dimethoxyethane, dimethyl sulfoxide, dimethylformamide, and hexamethylenephosphoric triamide.

The pH of the above aqueous medium is in the range of usually 9 to 13 (but not including 9), preferably 9.2~12, more preferably 9.5~11, during the reaction. In the case where the pH of the aqueous medium is 9 or below during the reaction, the catalyst is consumed as a rare earth element salt of the resulting product, so the etherification reaction does not run any more. On the other hand, in the case where the pH of the aqueous medium exceeds 13 during the reaction, the etherification reaction runs, but the reaction rate greatly decelerates.

In the production process of the present invention, the reaction is carried out in the aqueous medium, and there is no especial limitation, for example, in respect to the method to charge the raw compounds and the catalyst by adding them to the aqueous medium. However, examples of such a method include a method comprising the following sequential steps of: mixing the raw compounds and the aqueous medium; adjusting the pH of the aqueous medium below 6, preferably below 4; dissolving the catalyst; and further adding a basic substance to adjust the pH of the aqueous medium within the range of 9 to 13 (but not including 9).

If the use of a large amount of catalyst is permissible, it is permitted that the pH of the above aqueous medium is 9 or less.

Examples of the above basic substance include: alkaline metal hydroxides, such as sodium hydroxide and potassium hydroxide; and ammonium bases, such as ammonia, monoethylamine, diethylamine, and monoethanolamine. Particularly, sodium hydroxide is favorably used.

After the above adjustment of pH, the etherification reaction is carried out in that range of pH. This reaction is easily advanced by heating the reaction liquid to the temperature in the range of 40~150° C., preferably 70~120° C. The reaction is preferably carried out while the reaction liquid is sufficiently stirred.

The reaction pressure may be either normal or increased pressure. However, the reaction is usually carried out under normal pressure.

In the etherification step, the ether compound may be deposited in the course of the reaction of the raw compounds in the solvent. The deposition of the ether compound is, for example, carried out by adding a seed crystal, or by distilling off the reaction solvent, or by carrying out the addition of the seed crystal and the distilling-off of the reaction solvent at the same time.

The deposition of the ether carboxylate salt, which is a product, might naturally occur with the proceeding of the reaction, depending on the concentration during the reaction. However, when the deposition is carried out by adding a seed crystal or by concentrating the reaction liquid (e.g. by distilling off the solvent), the deposition is preferably carried out after the yield of the ether carboxylate salt has reached at least 50 weight %, further preferably at least 60 weight %, of the charged carboxyl-group-containing unsaturated organic compound or carboxyl-group-containing epoxy compound. The deposition by adding the seed crystal or by concentrating the reaction liquid is preferably carried out after the concentration of the ether carboxylate salt in the course of the reaction has reached at least 20 weight %, further preferably at least 30 weight %, most preferably at least 35 weight %.

When the above deposition is carried out using the seed crystal of the ether carboxylate salt, the deposition is, for example, carried out by adding the seed crystal in an amount of 0.005 weight % or more of the resultant ether carboxylate salt. The conditions, such as temperature, in adding the seed crystal are not especially limited.

The deposition of the ether carboxylate salt may be carried out by distilling off the reaction solvent including the aqueous medium, and is preferably carried out under such a reduced pressure that the above reaction temperature can be maintained. In the case where the temperature at which the reaction solvent is distilled off is too low, the viscosity of the reaction liquid rises so greatly that the stirring and mixing becomes difficult.

The deposition of the ether carboxylate salt by the above operation raises the concentration of the raw compounds, promotes the etherification reaction, and prevents side reactions from occurring. Especially, when the ether carboxylate salt is a salt having water of crystallization, the concentration of the raw compounds further rises, and the ether carboxylate salt can be obtained with a high yield.

After the above etherification reaction, the rare earth element can be separated and recovered in the form of a water-insoluble salt. Examples of this water-insoluble salt include carbonates and hydroxides of rare earth elements.

The carbonate of the rare earth element is, for example, obtainable by mixing the resultant reaction liquid with an alkaline carbonate after the reaction, thus converting the rare earth element ion, as included in the reaction liquid, into its carbonate, wherein examples of the alkaline carbonate include: carbonates of alkaline metals such as sodium, potassium, and lithium; carbonates of alkaline earth metals such as calcium and magnesium; carbonates of alkylamines such as monoethylamine, diethylamine, and triethylamine; carbonates of alkanolamines such as monoethanolamine, diethanolamine, and triethanolamine; carbonates of polyamines such as ethylenediamine and triethylenediamine; and ammonium carbonates such as ammonium carbonate. The amount of the above alkaline carbonate, as added, is at least a sufficient amount to convert the rare earth element ion into its carbonate, and the concrete amount thereof can easily be determined from the amount of the rare earth element ion as used. Incidentally, in such a case, it is preferable to mix the alkaline carbonate in such an amount that the pH of the reaction liquid will be at least 8. particularly, in the range of 9~14.

The method to mix the reaction liquid with the alkaline carbonate is not especially limited. Thus, a powder or aqueous solution of the alkaline carbonate may be added into the reaction liquid, or the reaction liquid may be added into a powder or aqueous solution of the alkaline carbonate. The temperature in the mixing is not especially limited, but is preferably the reaction temperature or lower, particularly, in the range of 40~90° C., for the purpose of suppressing the decomposition of the aimed ether carboxylate salt.

The carbonate of the rare earth element is hardly soluble in a neutral or alkaline aqueous solution containing the ether carboxylate salt (which is a reaction product), and therefore can easily be separated from the reaction liquid by conventional separation means such as filtration.

After the reaction, if the pH of the reaction liquid is adjusted within the range of 10~14, preferably 12~14, then the hydroxide of the rare earth element precipitates in the form of a hardly soluble solid and therefore can easily be separated from the reaction liquid by conventional separation means such as filtration.

The above water-insoluble salt, as separated from the reaction liquid, can be reused as a rare earth element source for a new etherification reaction, so the aforementioned etherification reaction can repeatedly be carried out.

In the present invention production process for an ether carboxylate salt, when glycolic acid and maleic acid are used as the hydroxyl-group-containing organic compound and the carboxyl-group-containing unsaturated organic compound respectively or when glycolic acid and epoxysuccinic acid are used as the hydroxyl-group-containing organic compound and the carboxyl-group-containing epoxy compound respectively, their chemical reaction formulae are illustrated below. Incidentally, in the formulae below, the carboxylate salt is represented as the corresponding carboxylic acid.

Reaction Between Glycolic Acid and Maleic Acid

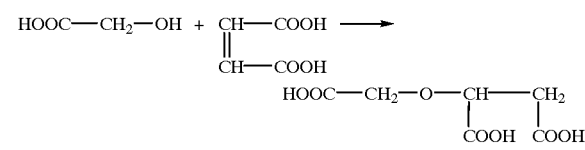

Reaction Between Glycolic Acid and Epoxysuccinic Acid

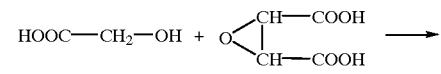

-continued

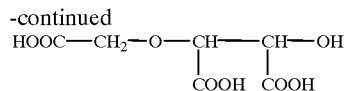

The ether carboxylate salt, as obtained by the process of the present invention, can easily be specified in accordance with the above formulae if the raw compounds are specified. Incidentally, the ether carboxylate salt, as obtained in this way, usually has the form in which part or all of carboxyl groups are, for example, displaced by carboxylate salt groups with alkaline metals, alkaline earth metals, alkylamines, alkanolamines, polyamines, or ammonia.

As is mentioned above, the ether carboxylate salt, as obtained above, particularly, sodium salt, is useful as a detergent builder and can be used for various detergent compositions, and further, as chelating agents.

(Effects and Advantages of the Invention)

In the present invention production process for an ether carboxylate salt, the aimed ether carboxylate salt is obtainable with a good yield and high selectivity, and the amount of expensive catalyst, as used, can be saved, and the recovery of the catalyst is easy.

The etherification reaction process of the present invention can suppress side reactions and thus give an ether compound with a high yield.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the below-mentioned examples.

EXAMPLE 1

An amount of 19.6 g of maleic anhydride was dissolved into 50 g of water. Then, 21.7 g of a 70 weight % aqueous glycolic acid solution and 1.6 g of lanthanum oxide (molar ratio to maleic anhydride: 0.025) were added thereto, and the resultant reaction liquid was stirred at room temperature until it became homogeneous. After this stirring, the pH of the reaction liquid was adjusted to 9.8 with sodium hydroxide to carry out a reaction at 80° C. for 10 hours. When the temperature of the reaction liquid fell to 60° C. after the end of the reaction, 3.2 g of sodium carbonate was added thereto, and the resultant mixture was stirred at 60° C. for 1 hour. Thereafter, the deposited solid (1) containing a major proportion of lanthanum carbonate was separated and recovered by filtration, and the resultant filtrate was analyzed by high performance liquid chromatography (HPLC). As a result, it was found that trisodium carboxymethoxysuccinate (CMOS-3Na) was obtained with a yield of 91.4 mol % (as based on the charged maleic anhydride). Incidentally, the identification of the CMOS-3Na was carried out by $^1$H-NMR and $^{13}$C-NMR. In addition, from results of analysis of the filtrate by ICP (inductively coupled plasma) emission spectrometry, it was found that the lanthanum ion concentration in the filtrate was 10 ppm or less, and that most of lanthanum constituting the lanthanum oxide was recovered as the solid (1).

EXAMPLE 2

An amount of 19.6 g of maleic anhydride was dissolved into 50 g of water. Then, 21.7 g of a 70 weight % aqueous glycolic acid solution and the entirety of the solid (1), as separated and recovered in Example 1, were added thereto, and the resultant reaction liquid was stirred at room temperature until it became homogeneous. After this stirring, the pH of the reaction liquid was adjusted to 9.8 with sodium hydroxide to carry out a reaction at 80° C. for 10 hours. After the end of the reaction, the same operation as of Example 1 was carried out to obtain trisodium carboxymethoxysuccinate (CMOS-3Na) with a yield of 90.8 mol % (as based on the charged maleic anhydride) in the filtrate. In addition, from results of analysis of the filtrate by ICP (inductively coupled plasma) emission spectrometry, it was found that the lanthanum ion concentration in the filtrate was 10 ppm or less, and that most of lanthanum constituting the lanthanum oxide was recovered as a solid.

EXAMPLE 3

An amount of 19.6 g of maleic anhydride was dissolved into 50 g of water. Then, 21.7 g of a 70 weight % aqueous glycolic acid solution and 0.1 g of lanthanum oxide (molar ratio to maleic anhydride: 0.0015) were added thereto, and the resultant reaction liquid was stirred at room temperature until it became homogeneous. After this stirring, the pH of the reaction liquid was adjusted to 9.8 with sodium hydroxide to carry out a reaction at 80° C. for 20 hours. When the temperature of the reaction liquid fell to 60° C. after the end of the reaction, 0.2 g of sodium carbonate was added thereto, and the resultant mixture was stirred at 60° C. for 1 hour. Thereafter, the deposited solid (3) containing a major proportion of lanthanum carbonate was separated and recovered by filtration, and the resultant filtrate was analyzed by high performance liquid chromatography (HPLC). As a result, it was found that trisodium carboxymethoxysuccinate (CMOS-3Na) was obtained with a yield of 80.3 mol % (as based on the charged maleic anhydride). Incidentally, the identification of the CMOS-3Na was carried out by $^1$H-NMR and $^{13}$C-NMR. In addition, from results of analysis of the filtrate by ICP (inductively coupled plasma) emission spectrometry, it was found that the lanthanum ion concentration in the filtrate was 10 ppm or less, and that most of lanthanum constituting the lanthanum oxide was recovered as the solid (3).

EXAMPLE 4

An amount of 19.6 g of maleic anhydride was dissolved into 50 g of water. Then, 21.7 g of a 70 weight % aqueous glycolic acid solution and the entirety of the solid (1), as separated and recovered in Example 1, were added thereto, and the resultant reaction liquid was stirred at room temperature until it became homogeneous. After this stirring, the pH of the reaction liquid was adjusted to 9.8 with sodium hydroxide to carry out a reaction at 80° C. for 20 hours. After the end of the reaction, the same operation as of Example 1 was carried out to obtain trisodium carboxymethoxysuccinate (CMOS-3Na) with a yield of 81.0 mol % (as based on the charged maleic anhydride) in the filtrate. In addition, from results of analysis of the filtrate by ICP (inductively coupled plasma) emission spectrometry, it was found that the lanthanum ion concentration in the filtrate was 10 ppm or less, and that most of lanthanum constituting the lanthanum oxide was recovered as a solid.

EXAMPLE 5

An amount of 19.6 g of maleic anhydride was dissolved into 50 g of water. Then, 21.7 g of a 70 weight % aqueous glycolic acid solution and 0.8 g of lanthanum oxide (molar ratio to maleic anhydride: 0.012) were added thereto, and the resultant reaction liquid was stirred at room temperature until it became homogeneous. After this stirring, the pH of the reaction liquid was adjusted to 9.8 with sodium hydroxide to carry out a reaction at 80° C. for 12 hours. When the temperature of the reaction liquid fell to 60° C. after the end of the reaction, sodium hydroxide was added thereto to adjust the pH of the reaction liquid to near 13, and the resultant mixture was stirred at 60° C. for 1 hour. Thereafter, the deposited solid (5) containing a major proportion of lanthanum hydroxide was separated and recovered by filtration, and the resultant filtrate was analyzed by high performance liquid chromatography (HPLC). As a result, it was found that trisodium carboxymethoxysuccinate (CMOS-3Na) was obtained with a yield of 84.5 mol % (as based on the charged maleic anhydride). Incidentally, the identification of the CMOS-3Na was carried out by $^1$H-NMR and $^{13}$C-NMR. In addition, from results of analysis of the filtrate by ICP (inductively coupled plasma) emission spectrometry, it was found that the lanthanum ion concentration in the filtrate was 10 ppm or less, and that most of lanthanum constituting the lanthanum oxide was recovered as the solid (5).

EXAMPLE 6

An amount of 19.6 g of maleic anhydride was dissolved into 50 g of water. Then, 21.7 g of a 70 weight % aqueous glycolic acid solution and the entirety of the solid (1), as separated and recovered in Example 1, were added thereto, and the resultant reaction liquid was stirred at room temperature until it became homogeneous. After this stirring, the pH of the reaction liquid was adjusted to 9.8 with sodium hydroxide to carry out a reaction at 80° C. for 12 hours. After the end of the reaction, the same operation as of Example 5 was carried out to obtain trisodium carboxymethoxysuccinate (CMOS-3Na) with a yield of 84.7 mol % (as based on the charged maleic anhydride) in the filtrate. In addition, from results of analysis of the filtrate by ICP (inductively coupled plasma) emission spectrometry, it was found that the lanthanum ion concentration in the filtrate was 10 ppm or less, and that most of lanthanum constituting the lanthanum oxide was recovered as a solid.

Comparative Example 1

An amount of 19.6 g of maleic anhydride was dissolved into 50 g of water. Then, 21.7 g of a 70 weight % aqueous glycolic acid solution and 1.6 g of lanthanum oxide (molar ratio to maleic anhydride: 0.025) were added thereto, and the resultant reaction liquid was stirred at room temperature until it became homogeneous. After this stirring, the pH of the reaction liquid was adjusted to 8.5 with sodium hydroxide to carry out a reaction at 80° C. for 10 hours. After the end of the reaction, the same operation as of Example 1 was carried out to obtain trisodium carboxymethoxysuccinate (CMOS-3Na) with a yield of 11.8 mol % (as based on the charged maleic anhydride) in the filtrate.

Comparative Example 2

An amount of 19.6 g of maleic anhydride was dissolved into 50 g of water. Then, 21.7 g of a 70 weight % aqueous glycolic acid solution and 0.8 g of lanthanum oxide (molar ratio to maleic anhydride: 0.012) were added thereto, and the resultant reaction liquid was stirred at room temperature until it became homogeneous. After this stirring, the pH of the reaction liquid was adjusted to 13.5 with sodium hydroxide to carry out a reaction at 80° C. for 12 hours. After the end of the reaction, the same operation as of Example 1 was carried out to obtain trisodium carboxymethoxysuccinate (CMOS-3Na) with a yield of 28.7 mol % (as based on the charged maleic anhydride) in the filtrate.

EXAMPLE 7

First, 29.4 g (0.3 mol) of maleic anhydride and 32.6 g (0.3 mol) of a 70 weight % aqueous glycolic acid solution were dissolved into 60 g of water, and then 2.4 g (0.0074 mol) of lanthanum oxide was added thereto. Next, while the resultant reaction mixture was stirred, sodium hydroxide was gradually added thereto to adjust the pH of the reaction mixture to 10, thus carrying out a reaction at 90° C. for 2 hours. Then, about 20 mg of a powder of sodium carboxymethoxysuccinate (CMOS) was added, and the reaction temperature was adjusted to 80° C. to continue the reaction. After the addition of the CMOS, the reaction mixture gradually got cloudy in white, and after about 8 hours, the reaction mixture was analyzed by high performance liquid chromatography (HPLC). As a result, it was found that CMOS was obtained with a yield of 94.8 mol % as based on the charged maleic anhydride.

EXAMPLE 8

An amount of 50 g of water was distilled off under reduced pressure from the reaction mixture as charged in the same way as of Example 7. Then, the reaction temperature was adjusted to 80° C. to initiate the reaction. After 2.5 hours from the initiation of the reaction, the deposition of crystals of CMOS began, and then the reaction was continued for 6 more hours. As a result, the CMOS was obtained with a yield of 95.6 mol % as based on the charged maleic anhydride.

Comparative Example 3

The reaction mixture of the same composition as of Example 7 was reacted at 90° C. for 2 hours in the same way as of Example 7. Then, the reaction was further continued at 80° C. for 6 hours without adding a seed crystal. The deposition of crystals was not seen in the course of the reaction. After the end of the reaction, the reaction mixture was analyzed by high performance liquid chromatography (HPLC). As a result, it was found that CMOS was obtained with a yield of 79 mol % as based on the charged maleic anhydride.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for an ether carboxylate salt, comprising the etherification step of reacting a hydroxyl-group-containing organic compound and a carboxyl-group-containing organic compound in an aqueous medium in the presence of a catalyst containing a rare earth element, thus obtaining the ether carboxylic acid, wherein the carboxyl-group-containing organic compound is at least one compound selected from the group consisting of carboxyl-group-containing unsaturated organic compounds and carboxyl-group-containing epoxy compounds;

with the process being characterized in that the pH of the aqueous medium is in the range of 9~13, but not including 9, and in that the amount of the catalyst, as used, is in the range of 0.0001~0.4 mol per 1 mol of the carboxyl-group-containing organic compound.

2. A production process for an ether carboxylate salt according to claim 1, further comprising the step of separating and recovering the rare earth element in the form of a water-insoluble salt after the reaction.

3. A production process for an ether carboxylate salt according to claim 2, wherein the water-insoluble salt is a carbonate and/or hydroxide.

4. A production process for an ether carboxylate salt according to claim 2, further comprising the step of reusing the water-insoluble salt as the catalyst.

5. A production process for an ether carboxylate salt according to claim 1, further comprising the step of depositing the resultant ether carboxylic acid or its salt in the course of the reaction to promote the reaction.

6. A production process for an ether carboxylate salt according to claim 5, further comprising the step of adding a seed crystal into the resultant reaction liquid to deposit the resultant ether compound.

7. A production process for an ether carboxylate salt according to claim 5, further comprising the step of distilling off the solvent to deposit the resultant ether compound.

8. A production process for an ether carboxylate salt according to claim 1, wherein the hydroxyl-group-containing organic compound is glycolic acid, and wherein the carboxyl-group-containing organic compound is maleic acid.

9. A production process for an ether carboxylate salt according to claim 1, wherein the amount of the catalyst, as used, is in the range of 0.0005–0.25 mol per 1 mol of the carboxyl-group-containing organic compound.

10. A production process for an ether carboxylate salt according to claim 1, wherein during said etherification reaction, said process further comprises the step of adding a seed crystal into the resultant reaction liquid and depositing the resultant ether carboxylic acid or its salt to promote said etherification reaction.

11. A production process for an ether carboxylate salt according to claim 1, wherein during said etherification reaction, said process further comprises the step of distilling off the solvent and depositing the resultant ether carboxylic acid or salt to promote said etherification reaction.

* * * * *